United States Patent

Patil et al.

(10) Patent No.: US 7,429,684 B2
(45) Date of Patent: Sep. 30, 2008

(54) PROCESS FOR OLIGOMERIZATION OF ETHYLENE TO LINEAR α-OLEFINS

(75) Inventors: Abhimanyu O. Patil, Westfield, NJ (US); Stephen Zushma, Clinton, NJ (US)

(73) Assignee: ExxonMobile Research and Engineering Company, Annandale, NJ (US)

( * ) Notice: Subject to any disclaimer, the term of this patent is extended or adjusted under 35 U.S.C. 154(b) by 654 days.

(21) Appl. No.: 11/037,982

(22) Filed: Jan. 18, 2005

(65) Prior Publication Data

US 2005/0192470 A1 Sep. 1, 2005

Related U.S. Application Data

(60) Provisional application No. 60/548,654, filed on Feb. 27, 2004.

(51) Int. Cl.
*C07C 2/02* (2006.01)
*B01J 31/00* (2006.01)

(52) U.S. Cl. .......... 585/523; 585/522; 585/531; 585/532; 502/152; 502/167; 502/171

(58) Field of Classification Search ......... 585/511–513, 585/522, 523, 531, 532; 502/152, 167, 171
See application file for complete search history.

(56) References Cited

FOREIGN PATENT DOCUMENTS

| | | | |
|---|---|---|---|
| EP | 1125928 | A1 | 8/2001 |
| WO | WO0200339 | A2 | 3/2002 |
| WO | WO03072529 | A1 | 4/2003 |

*Primary Examiner*—Glenn Caldarola
*Assistant Examiner*—In Suk Bullock
(74) *Attorney, Agent, or Firm*—Robert A. Migliorini

(57) ABSTRACT

A process for preparing α-olefins from ethylene wherein the α-olefins are substantially free of olefins having greater than 12 carbon atoms comprises contacting ethylene under oligomerization conditions with a 2,6-bis(phenylimino) pyridyl metal halide catalyst in which the metal is Fe, Ni, Co or Pd.

7 Claims, No Drawings

PROCESS FOR OLIGOMERIZATION OF ETHYLENE TO LINEAR α-OLEFINS

This application claims the benefit of U.S. Ser. No. 60/548,654 filed Feb. 27, 2004.

FIELD OF INVENTION

The present invention relates to the preparation of linear α-olefins from ethylene. More particularly the present invention is concerned with improvements in the oligomerization of ethylene to selectively produce increased amounts of $C_4$ to $C_{10}$ linear α-olefins.

BACKGROUND OF INVENTION

Linear α-olefins are versatile intermediates in the preparation of a wide range of chemical products. For example, $C_4$-$C_8$ α-olefins are used as co-monomers with ethylene in copolymer formation, $C_{12}$-$C_{20}$ α-olefins are used as feedstock in surfactant formation and $C_6$-$C_{10}$ α-olefins are used as feedstocks for plasticizer formation.

Most commercially produced α-olefins are made by the oligomerization of ethylene in the presence of catalysts that tend to produce a mixture of α-olefins ranging from $C_4$ to $C_{30}$ and beyond. Examples of such commercially used catalysts include certain nickel-phosphine complexes, alkylaluminum compounds, and titanium halide with a Lewis acid.

In U.S. Pat. No. 6,103,946, for example, α-olefins are prepared from ethylene with an iron complex of a selected 2,6-pyridine dicarboxaldehyde bisimine and in some cases a selected activator such as an alkyl aluminum compound. The Schulz-Flory distribution (See B. Elvers, et al., Ed. Ullmann's Encyclopedia of Industrial Chemistry, Vol. A13, VCH Verlagsgesellschaft mbH Weinheim, 1989, p. 243-247 and 275-276) for the mixture of olefins prepared by that process is in the range of 0.7 to 0.87. The Schulz-Flory distribution is defined as:

α=n($C_{n+2}$ olefin)/n($C_n$ olefin) wherein n($C_n$ olefin) is the moles of olefin containing n carbon atoms and n($C_{n+2}$ olefin) is the moles of olefin containing n+2 carbon atoms. For α values in the range of 0.70 to 0.87 the α-olefins are in the $C_4$ to $C_{20}$ and greater range.

Britovsek et al in Chem. Eur. J. 2000, 6, No. 12 pages 2221-2231 disclose the oligomerization of ethylene with a series of bis(imino)pyridyliron and cobalt complexes containing imino-aryl rings with methyl substituents in various positions on the aryl rings. In the majority of instances the α-values obtained were in the 0.63 to 0.79 range. In one instance in which the catalyst had only one methyl group in the ortho position the resulting mixture had an α-value of 0.50 with oligomer carbon numbers in the mixture ranging up to about 22.

Because the market demand for individual α-olefins making up these mixtures is not the same it would be useful to be able to vary the distribution to produce those olefins which are in greater demand which presently are those in the $C_4$ to $C_{10}$ range.

One object of the present invention is to produce linear a olefins from ethylene with an α-value of below about 0.45.

Another object is to produce substantial amounts of linear α-olefins from ethylene having carbon contents of from about $C_4$ to about $C_{10}$ and no α-olefins greater than $C_{12}$.

These and other objects will become apparent from the description of the invention which follows.

SUMMARY OF INVENTION

According to one embodiment of the present invention there is provided a process for producing α-olefins from ethylene wherein the α-olefins produced are substantially free of olefins having greater than 12 carbon atoms. The process comprising contacting ethylene under oligomerization conditions with (a) an oligomerization catalyst having the formula where M is Fe, Ni, Co or Pd; and X is a halogen; and (b) an activating co-catalyst.

Other embodiments will become apparent from the detailed description.

DETAILED DESCRIPTION OF THE INVENTION

The process of the present invention is concerned with the oligomerization of ethylene to produce a mixture of α-olefins that is substantially free of olefins having greater than 12 carbon atoms. Indeed, the present invention provides α-olefins having an α-value of about 0.45 and less. Preferably the α-olefins produced are in the $C_4$ to $C_{12}$ range with not more than 0.5 mole % of the mixture being a $C_{12}$ olefin.

The process of the invention is carried out by contacting ethylene under oligomerization conditions with (a) a catalyst having the formula

I where M is Fe, Ni, Co or Pd; and X is a halogen; and (b) an activating co-catalyst.

In a preferred embodiment M is Fe, and X is bromine or chlorine.

Compounds of formula I may be prepared by reacting a compound of formula II

II with a compound having the formula $MX_2$ where M and X are as described above.

A compound of formula II may be prepared by reacting a compound of formula III

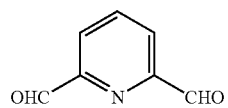

with a compound or mixture of compounds of the formula IV

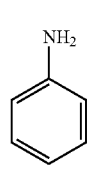

The activating co-catalyst is selected from aluminoxanes which are well known in the art. Typically aluminoxanes are prepared by the controlled addition of water to an alkylaluminum compound such as trimethylaluminum. Indeed methyl aluminoxane, MAO, is the preferred co-catalyst. The ratio of metal complex to activating co-catalyst is from $1:10^{-2}$ to $1:10^6$.

In the process ethylene is contacted with the catalyst and activating co-catalyst under oligomerization conditions. Such conditions include temperatures in the range of about 0° C. to about 100° C., ethylene pressures in the range of about 15 to 2000 psig for times ranging from about 1 minute to 24 hours.

In one embodiment the oligomerization is conducted in the presence of an inert solvent. Suitable solvents include toluene, ethylene, propane, butane, pentane, hexane, methylene chloride, carbon dioxide, and mixture thereof. Toluene is preferred.

In another embodiment the ethylene oligomerization is conducted by supporting the catalyst and activating co-catalyst on a porous carrier such as alumina, silica, cross-linked polymers and the like and contacting the supported catalyst with ethylene.

The invention is further illustrated by the following Examples and Comparative Examples.

EXAMPLE 1

Synthesis of 2,6-bis(phenylimino) pyridine

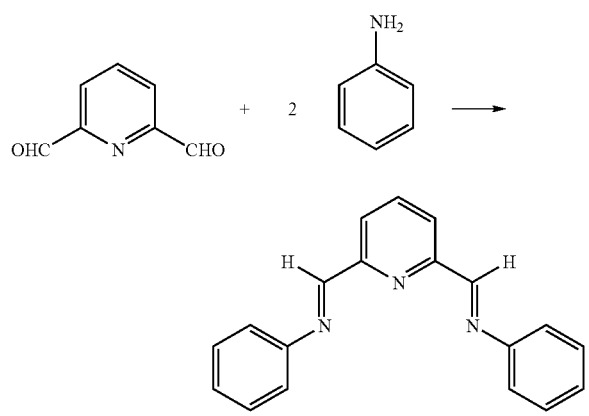

2,6-pyridine dicarboxaldehyde (0.3071 g, 2.3 mmol) was added to a solution of aniline (0.5292 g, 5.7 mmol) in absolute ethanol (20 mL) at room temperature. 0.5 mL of formic acid was then added to the above solution. The mixture was stirred at room temperature for 65 hours. The product was filtered, washed with cold ethanol and dried in a vacuum oven (50° C.) overnight. Yield 0.2245 g (34.2%).

EXAMPLE 2

Synthesis of 2,6-bis(phenylimino)pyridyliron(II) chloride

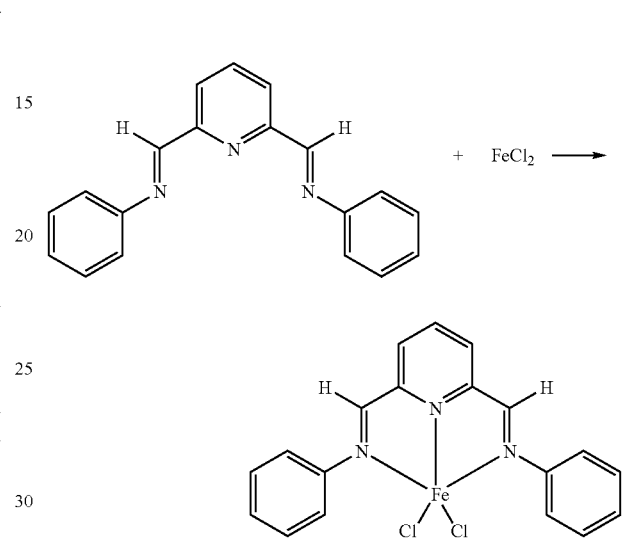

$FeCl_2$ (0.0666 g, 0.5 mmol) was dissolved in hot n-butanol (20 mL) at 80° C. A suspension of 2,6-bis(phenylimino) pyridine (0.15 g, 0.5 mmol) in n-butanol was added dropwise at 80° C. After stirring at 80° C. for 30 min, the reaction mixture was allowed to cool to room temperature and stirred overnight. The reaction volume was reduced to a 3 mL and diethyl ether was added to precipitate the product, which was subsequently washed three times with diethyl ether and dried in vacuum oven. Yield: 0.1701 g (87.5%).

EXAMPLE 3

Ethylene Oligomerization Using the Catalyst of Example 2

In an argon glovebox a toluene suspension was prepared in a 50 ml Parr glass liner by adding 2,6-bis(phenylimino)pyridyliron(II) chloride complex (6.3 mg, FW 370.07, $1.7 \times 10^{-2}$ mmoles) (product of Example 2) in 1 mL methylene chloride followed by 15 mL toluene and 2.044 g of 30% MAO solution in toluene (Al/Fe=621). In the glovebox, the glass liner was placed into the Parr reactor. The reactor was transfer to a hood containing the controller for the reactor. The reactor was pressurized with 500 psig of ethylene. The solution was stirred (stirring rate 500 RPM) at 25° C. for 30 minutes. The unreacted ethylene was vented to obtain the product. The product was analyzed by GC and by gas chromatography-mass spectrometry. GC analysis of the product shows peaks due to α-olefins up to $C_{12}$. The detailed analysis of the individual α-olefins is given in Table I. The α value was found to be 0.4. There was no solid polymer formed in this reaction.

TABLE I

| | Olefin Distribution | |
|---|---|---|
| α-olefin | Wt % | Mole % |
| $C_4$ | 61 | 72.5 |
| $C_6$ | 25.5 | 20.1 |
| $C_8$ | 9.0 | 5.3 |
| $C_{10}$ | 3.3 | 1.5 |
| $C_{12}$ | 1.2 | 0.5 |

What is claimed is:

1. A method for producing α-olefins from ethylene wherein the α-olefins are substantially free of α-olefins having greater than 12 carbon atoms, the method comprising:
   contacting ethylene under oligomerization conditions with
   (a) a catalyst having the formula

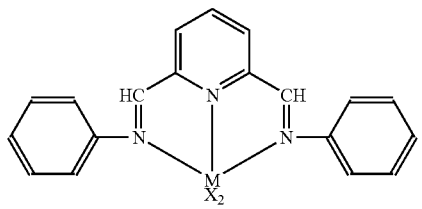

wherein M is Fe, Ni, Co or Pd, and X is halogen; and
   (b) an activating co-catalyst.

2. The method of claim 1 wherein the activating co-catalyst is an aluminoxane.

3. The method of claim 2 wherein the contacting is at a temperature in the range of about 0° C. to about 100° C. and at an ethylene pressure of about 15 to about 2000 psig.

4. The method of claim 3 wherein the contacting is conducted in the presence of an inert solvent.

5. The method of claim 4 wherein M is Fe and X is Cl.

6. A method for forming liner α-olefins from ethylene wherein the α-olefins have an α-value of 0.45 and lower, the method comprising contacting ethylene with a catalyst and an activating co-catalyst, said catalyst having the formula

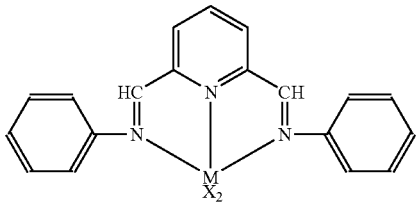

wherein M is Fe, Ni, Co or Pd and X is halogen,
said activating co-catalyst being an aluminoxane,
said contacting being at a temperature in the range of 0 to 100° C., an ethylene pressure in the range of 15 to 2000 psig for about 1 minute to about 24 hours,
whereby linear α-olefins are produced having an α-value of 0.45 and lower.

7. The method of claim 6 wherein M is Fe and X is Cl.

* * * * *